United States Patent [19]

Sato et al.

[11] Patent Number: 4,952,564
[45] Date of Patent: Aug. 28, 1990

[54] ANTIALLERGIC AGENT

[75] Inventors: Toshio Sato; Hitoshi Matsumoto, both of Tokushima, Japan

[73] Assignees: Dainippon Ink and Chemicals, Inc.; Nippon Hypox Laboratories Incorporated, both of Tokyo, Japan

[21] Appl. No.: 110,709
[22] PCT Filed: Mar. 9, 1987
[86] PCT No.: PCT/JP87/00143
§ 371 Date: Sep. 23, 1987
§ 102(e) Date: Sep. 23, 1987
[87] PCT Pub. No.: WO87/05215
PCT Pub. Date: Sep. 11, 1987

[30] Foreign Application Priority Data

Mar. 8, 1986 [JP] Japan .................................. 61-49530

[51] Int. Cl.$^5$ .................... A61K 31/12; A61K 31/35
[52] U.S. Cl. .................................. 514/57; 514/546; 514/533; 514/826
[58] Field of Search ................ 514/57, 546, 533, 826; 424/195.1; 536/18.1

[56] References Cited

U.S. PATENT DOCUMENTS

| | | | |
|---|---|---|---|
| 3,928,421 | 12/1975 | Kyogoku et al. | 514/927 |
| 4,083,994 | 4/1978 | Noda et al. | 514/546 |
| 4,085,135 | 4/1978 | Kyogoku et al. | 514/926 |
| 4,219,569 | 8/1980 | Glenn | 514/685 |
| 4,374,284 | 2/1983 | Shibata et al. | 514/927 |
| 4,410,546 | 10/1983 | Noda et al. | 514/568 |
| 4,428,876 | 1/1984 | Iwamura | 536/128 |
| 4,656,305 | 4/1987 | Vanstone et al. | 514/533 |
| 4,678,772 | 7/1987 | Segal et al. | 536/18.1 |
| 4,753,965 | 6/1988 | Stemerick et al. | 514/647 |

FOREIGN PATENT DOCUMENTS

| | | |
|---|---|---|
| 2810253 | 9/1978 | Fed. Rep. of Germany . |
| 2383157 | 10/1978 | France . |
| 60-177815 | 9/1985 | Japan . |
| 60-178815 | 12/1985 | Japan . |
| 61-60609 | 3/1986 | Japan . |
| 61-76433 | 4/1986 | Japan . |
| 62-185037 | 8/1987 | Japan . |
| 1566497 | 4/1980 | United Kingdom . |

OTHER PUBLICATIONS

*Shin Yakuzaigaku Soron,* (Introduction to Modern Pharmaceutics), 3rd Ed., p. 20 (1987), Nankodoco Ltd., Tokyo-partial translation.
*Kagaku Daijiten,* (Encyclopaedia Chimica), vol. 8, pp. 1016 and 342 (1962), partial translation.
*Kagaku Daijiten* (Encyclopaedia Chimica), vol. 9 (1962), p. 589, Re: "Carbowax".
*Taisha,* vol. 10, pp. 619–625 (1973), Shibata et al and partial translation.
*The American Journal of Medicine,* Feb. 22, 1988, vol. 84 (Suppl.2A), pp. 41–48, Kevin J. Ivey, M.D.
*Biochem. Pharmacol.,* vol. 33, No. 21 (1984) pp. 3333–3338.
*J. Inst. Chemists,* vol. 53, Sep. 1981, pp. 234–236.
*Prostaglandins,* vol. 30, No. 3, Sep. 1985.
*Chemical Abstract,* vol. 102, No. 23, 199302(c) Jun. 10, 1985.
Fifth Medicinal Chemical Symposium-Preliminary Publication p. 68 (1983).
*Ensho,* 4 (4) p. 554, Nakadate et al. (in Japanese).
Chemical Abstracts, vol. 102, No. 23, Abstract No. 199302c (Chem. Abstr. 102:199302c), Jun. 10, 1985 (10/06/85) Columbus, Ohio, U.S.A.) Nakadate T., et al., Ensho in Japanese 4(4), 554.

*Primary Examiner*—Ronald W. Griffin
*Attorney, Agent, or Firm*—Oblon, Spivak, McClelland, Maier & Neustadt

[57] ABSTRACT

The present invention which is an antiallergic agent characterized by containing isoliquiritigenin as an effective component provides a novel antiallergic agent exhibiting a low toxicity and excellent antiallergic properties.

6 Claims, No Drawings

4,952,564

ANTIALLERGIC AGENT

TECHNICAL FIELD

The present invention relates to a novel antiallergic agent.

BACKGROUND ART

It has been reported that isoliquiritigenin, contained in an extract of Glycyrrihiza, exhibits an antiulcerous activity, and is used in the treatment of gastric ulcers (Japanese Patent Publication No. 8485/1973). However, it has previously been not known at all that isoliquiritigenin has the activity of ameliorating allergosis.

DISCLOSURE OF INVENTION

As a result of earnest investigations, the inventors of the present invention newly discovered that isoliquiritigenin has an excellent antiallergic activity and produces few side effects when administered for a long time, leading to the achievement of the present invention.

In other words, the present invention relates to an antiallergic agent containing isoliquiritigenin as an effective component.

Isoliquiritigenin according to the present invention can be provided as its salt, if necessary.

In accordance with the present invention, isoliquiritigenin can be orally or parenterally administered as an anti I-type allergic agent (e.g., by venous injection, hypodermic administration, or rectal administration) in order to cure, treat, and prevent asthma, allergic dermal diseases, ectopic and atopic dermatitis, allergic rhinitis, urticaria, and food allergies and can be prepared in a form suitable for each of these administration method. For example, such a medicine can be prepared by a known method with the addition of additives such as an atoxic excipient, binder, lubricant, disintegrator, antiseptic agent, isotonizing agent, stabilizer, dispersant, antioxidant, coloring agent, flavoring agent, or buffer.

Such a medicine can be prepared in any preparation form, such as a tablet, a capsule, granules, powder, fine granules, a pill, a troche, a suppository, an ointment, an injection agent, an emulsion, a suspension, or a syrup, corresponding to the use thereof. Examples of the above-described usable atoxic additives include starch, gelatine, glucose, lactose, fructose, maltose, magnesium carbonate, talc, magnesium stearate, methyl cellulose, carboxymethyl cellulose, gum arabic, polyethyleneglycol, propyleneglycol, petrolatum, Carbowax, glyceline, ethanol, simple syrup, i.e., concentrated sucrose solution in water, sodium chloride, sodium sulfite, sodium phosphate, citric acid, polyvinyl pyrolidone, and water. This preparation can include other medicines which are therapeutically useful.

The content of isoliquiritigenin in this medicine depends upon the form thereof, but it is preferable that the medicine generally contains it in a concentration of 0.1 to 100 wt %.

It is possible to widely vary the dosage of the medicine of the present invention in accordance with the kind of warm-blooded animal including humans, to which the medicine is applied, the severity of symptoms, and the diagnosis of the doctor, but the dosage can generally be determined to be 0.01 to 300 mg/kg per day. However, it is possible to change the dosage range to correspond to the severity of the symptoms of the patient and the diagnosis of the doctor. The above-described dosage can be divided into one or more portions so that the medicine can be administered one or more times a day.

BEST MODE FOR CARRYING OUT THE INVENTION

The present invention is described below on the basis of examples of the pharmaceutical effects thereof and of prescription. However, as a matter of course, these examples do not limit the present invention.

EXAMPLE 1

(Toxicity)

Isoliquiritigenin was orally or intra-peritoneally administered to five 5-week-old ddY male mice. Consequently, it was determined that the minimum lethal dose was not less than 3000 mg/kg (oral administration) or not less than 1000 mg/kg (intra-peritoneal administration).

EXAMPLE 2

(Antiallergic Activity)

The Schultz-Dale test and the inhibition effect of the compound of the present invention on the liberation of histamines by a compound 48/80 indicate that isoliquiritigenin has an antiallergic activity.

1. Schultz-Dale reaction (1) Active sensitization of guinea pig by antigenic egg-white albumin (EWA)

A physiological saline solution of 10 mg/kg of EWA was mixed with complete Freund's adjuvant to form an equivalent mixed emulsion, and this emulsion was dispersively administered at a rate of 0.2 ml/100 g into the femoral muscle of a male guinea pig of the Hartley-type which had a body weight of about 300 g. After 1, 2 and 3 weeks, additional sensitization was conducted by injecting an equivalent mixed emulsion of a physiological saline solution of 4 mg/ml of EWA and complete Freund's adjuvant into the muscle at a ratio of 0.1 ml/100 g and the guinea pig was subjected to the Schultz-Dale reaction one week after the final sensitization.

(2) Schultz-Dale reaction

The ileum of the guinea pig which was actively sensitized in (1) above was extirpated and immediately soaked in Tyrode's solution to form a specimen of a length of 15 mm which was suspended at a tensile force of 1.5 g in a Magnus' tube (10 ml) kept at a temperature of 37° C. Contraction of the ileum by $10^{-6}$ mole of histamine. 2HCl was repeated several times, and a physiological saline solution of isoliquiritigenin containing 0.2% sodium bicarbonate was added thereto when the contraction had became constant. Then, after preincubation for about 2 minutes, 10 μg/ml of EWA was added to the Magnus' tube and the contraction of the ileum was recorded. As a control, the contraction of the ileum was measured by an operation which was similar to that of the above, except that the physiological saline solution of isoliquiritigenin containing 0.2% sodium bicarbonate was not applied. The results obtained are shown in Table 1. The contraction ratio is the value when the contraction ratio at $10^{-6}$ mole of histamine is taken to be 100%.

TABLE 1

| Specimen | Contraction ratio (%) | Inhibition ratio (%) |
| --- | --- | --- |
| Control | 104.1 | — |
| Substance of this invention ($10^{-4}$ mole) | 10.4 | 90.2 |

It is clear from the above results that isoliquiritigenin inhibits the contraction of the ileum of the guinea pig by histamine and SRS-A.

2. Inhibition effect of the medicine on the liberation of histamine by compound 48/80.

(1) Preparation of rat peritoneal exudation cells 10 ml of Locke's solution containing 0.1% of bovine serum albumin was injected into the abdominal cavity of a rat which had been killed by exsanguination. The rat was lightly massaged, then subjected to an abdominal section so that an abdominal solution was collected. The abdominal cavity was also washed with 5 ml of the same solution and the washing solution was collected and mixed with the above abdominal solution. The abdominal solution was centrifuged at 500 rpm for 5 minutes, then 5 ml of cool Locke's solution was added to the sediment. After the sediment had been washed, 3 ml of cool Locke's solution was again added thereto to form a solution of rat peritoneal exudation cells.

(2) Inhibition effect of medicine on the liberation of histamine by compound 48/80.

0.5 ml of Locke's solution and 1.0 ml of each of the solutions of isoliquiritigenin prepared to the concentration shown in Table 2 (the isoliquiritigenin was dissolved in a physiological saline solution containing 1% sodium bicarbonate, the resultant solution being diluted with Locke's solution) were added to 0.3 ml of the solution of rat peritoneal exudation cells obtained in (1) above and were incubated at 37° C. for 5 minutes. Then, 0.2 ml each of a Locke's solution of the compound 48/80 (1 mg/100 ml) was added to the solution and the mixture was incubated at 37° C. for 10 minutes. After the reaction was stopped by cooling, the obtained solution was centrifuged at 2,500 rpm for 10 minutes to be separated into 1.7 ml of supernatant and 0.3 ml of sediment. 0.1 ml of water and 0.2 ml of 100% trichloroacetic acid were added to the supernatant, and 1.5 ml of Locke's solution and the 100% trichloroacetic acid were added to the sediment which was then allowed to stand for 30 minutes at room temperature and was centrifuged at 3,000 rpm for 15 minutes. 0.35 ml of each of the supernatant and the supernatant of the sediment was taken and 1.65 ml of water and 0.4 ml of 1N sodium hydroxide were added in turn to each of the supernatants. 0.1 ml of 0.5% OPT (orthophthalaldehyde) methanol solution was added to each of the resultant solutions which were then allowed to react at room temperature for 4 minutes. After the reaction was stopped by the addition of 0.2 ml of 2M citric acid, the fluorescence of each of the reaction solutions was measured by a fluorophotometer.

As a control, Locke's solution was added instead of the solution of isoliquiritigenin and, as a blank, the Locke's solution was added instead of isoliquiritigenin and the compound 48/80, the other operations being the same as those described above.

The inhibition ratio of isoliquiritigenin for the liberation of histamine by the compound 48/80 is calculated from the following equations:

$$\text{Liberation ratio of histamine (\%)} = \frac{P_s}{P_s + P_r} \times 100 = A$$

$P_s$: amount of free histamines (in the supernatant)
$P_r$: amount of remaining histamines (in the sediment)

$$\text{Inhibition ratio (\%)} = 100 - \frac{I - B}{C - B} \times 100$$

$I$: value $A$ of isoliquiritigenin
$C$: value $A$ of the control
$B$: value $A$ of the blank

TABLE 2

| Concentration of isoliquiritigenin (mg/ml) | Liberation ratio of histamine (%) | Inhibition ratio (%) |
| --- | --- | --- |
| Control | 87.4 | — |
| 100 | 71.0 | 21 |
| 300 | 32.7 | 70 |
| 1000 | 9.2 | 100 |
| Blank | 9.3 | — |

It is clear from the above results that isoliquiritigenin inhibits histamines from liberating mast cells by the compound 48/80.

As can be seen from the above-described results of pharmaceutical experiments, the isoliquiritigenin of the present invention exhibits an excellent antiallergic activity on I-type allergies and has a very low toxicity, and hence it is useful as a medicine.

EXAMPLE 3

Tablets containing either 5 mg or 25 mg of isoliquiritigenin per tablet were prepared in accordance with the following prescriptions.

| Prescription example 1 | 5 mg tablets |
| --- | --- |
| Isoliquiritigenin | 5 |
| Lactose | 137 |
| Starch | 45 |
| Carboxymethyl cellulose calcium | 10 |
| Talc | 2 |
| Magnesium stearate | 1 |
| | 200 mg/tablet |

| Prescription example 2 | 25 mg tablets |
| --- | --- |
| Isoliquiritigenin | 25 |
| Lactose | 120 |
| Starch | 42 |
| Carboxymethyl cellulose calcium | 10 |
| Talc | 2 |
| Magnesium stearate | 1 |
| | 200 mg/tablet |

The detailed method of preparation is given below.

Crystals of isoliquiritigenin were ground and lactose and starch were added thereto and mixed. 10% of a starch paste was added to the mixture which was agitated to form granules. After drying, granules were graded by size to about 850μ, talc and magnesium stearate were mixed with the granules, and tablets were made therefrom.

| Prescription example 3 | 20 mg capsules |
| --- | --- |
| Isoliquiritigenin | 20 |
| Lactose | 53 |
| Starch | 25 |

| -continued | |
|---|---|
| Prescription example 3 | 20 mg capsules |
| Magnesium stearate | 2 |
| | 100 mg |

Isoliquiritigenin was well ground, starch, lactose, and magnesium stearate were added thereto and well mixed, and the mixture was charged into capsules.

EXAMPLE 4

Injection solution

| Isoliquiritigenin | 10 mg |
|---|---|
| Macrogol 4000 | 25 mg |
| sodium chloride | 9 mg |

Distilled water for injection use was added to this solution until the total volume was 1 ml.

Isoliquiritigenin was dissolved in distilled water containing Macrogol 4000, the amount of sodium chloride shown in the prescription was added and the pH of the mixture was adjusted to be about 7.0. The resultant solution was charged in ampules and sealed therein.

Industrial Applicability

The antiallergic agent of the present invention, containing isoliquiritigenin as an effective component, can provide an antiallergic agent of low toxicity which has excellent antiallergic properties.

What is claimed is:

1. A method for the treatment and prevention of allergic diseases, comprising administering to a mammal in need of such treatment or prevention a medicine containing a therapeutically effective amount for the treatment of allergic diseases of isoliquiritigenin "or a pharmaceutically acceptable salt thereof".

2. A method as claimed in claim 1, wherein said medicine further comprises as an additive at least one substance selected from the group consisting of atoxic excipient, binder, lubricant, disintegrator, antiseptic agent, isotonizing agent, stabilizer, dispersant, antioxidant, coloring agent, flavoring agent, and buffer.

3. A method as claimed in claim 2, wherein said additive is at least one compound selected from the group consisting of starch, gelatin, glucose, lactose, fructose, maltose, magnesium carbonate, talc, magnesium stearate, methyl cellulose, gum arabic, polyethylene glycol, propylene, petrolatum, glycerin, ethanol, simple syrup, sodium chloride, sodium sulfite, sodium phosphate, citric acid, polyvinyl pyrrolidone, and water.

4. A method as claimed in any one of claims 1 to 3, wherein said medicine contains isoliquiritigenin or a pharmaceutically acceptable salt thereof in an amount of at least 0.1 wt. %.

5. A method as claimed in claim 1, wherein said medicine is administered by oral or parenteral administration.

6. A method as claimed in claim 5, wherein said parenteral administration is venous injection, hypodermic administration, or rectal administration.

* * * * *

UNITED STATES PATENT AND TRADEMARK OFFICE
CERTIFICATE OF CORRECTION

PATENT NO. :   4,952,564
DATED      :   AUGUST 28, 1990
INVENTOR(S) :  TOSHIO SATOH ET AL.

It is certified that error appears in the above-identified patent and that said Letters Patent is hereby corrected as shown below:   Title page:

The first inventor's name is incorrectly spelled. Please delete "Sato" and insert --Satoh--.

Signed and Sealed this

Tenth Day of March, 1992

Attest:

HARRY F. MANBECK, JR.

Attesting Officer

Commissioner of Patents and Trademarks